(12) United States Patent
Kuhen et al.

(10) Patent No.: US 7,604,977 B2
(45) Date of Patent: Oct. 20, 2009

(54) METHODS AND COMPOSITIONS FOR INHIBITING HIV INFECTION

(75) Inventors: Kelli L. Kuhen, Waltham, MA (US); Jeremy S. Caldwell, La Jolla, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 11/408,551

(22) Filed: Apr. 21, 2006

(65) Prior Publication Data

US 2006/0286036 A1 Dec. 21, 2006

Related U.S. Application Data

(60) Provisional application No. 60/673,623, filed on Apr. 21, 2005.

(51) Int. Cl.
*C12N 7/00* (2006.01)
*C07H 21/04* (2006.01)

(52) U.S. Cl. .................................. 435/235.1; 536/24.5

(58) Field of Classification Search .................. None
See application file for complete search history.

(56) References Cited

U.S. PATENT DOCUMENTS

2004/0191905 A1* 9/2004 Stevenson et al. ............ 435/375

* cited by examiner

*Primary Examiner*—Bruce Campell
*Assistant Examiner*—Nicole Kinsey White
(74) *Attorney, Agent, or Firm*—Timothy L. Smith, J.D.; Genomics Institute of the Novartis Research Foundation

(57) ABSTRACT

This invention provides novel methods for identifying agents that inhibit HIV infection. The anti-HIV agents are identified by screening test compounds for ability to modulate a biological activity of isopeptidase T (IsoT), e.g., its isopeptidase activity or its binding to another molecule such as viral protein R (Vpr). Such IsoT modulators can be further examined for their activity in inhibiting an activity indicative of HIV infection or HIV replication. These novel anti-HIV agents are useful in the prevention or treatment of HIV infection and conditions associated with or caused by HIV infection.

5 Claims, 5 Drawing Sheets

Isopeptidase T prey clone (PL) structure

Isopeptidase T ORF (FL) structure (pancreas-derived cDNA library)

B ized. In some preferable

METHODS AND COMPOSITIONS FOR INHIBITING HIV INFECTION

CROSS-REFERENCE TO RELATED APPLICATIONS

This application claims the benefit of priority under 35 U.S.C. §119(e) to U.S. Provisional Patent Application No. 60/673,623, filed Apr. 21, 2005. The disclosure of the priority application is incorporated herein by reference in its entirety and for all purposes.

FIELD OF THE INVENTION

The present invention generally relates to methods for identifying compounds that inhibit HIV infection and therapeutic applications of such compounds. More particularly, the invention pertains to screening for inhibitors of isopeptidase T (IsoT), and to methods of using such inhibitors to treat or prevent HIV infections.

BACKGROUND OF THE INVENTION

Human immunodeficiency viruses (HIV) are lentiviruses from the family of retroviridae. It was estimated that transmission of HIV through sexual contact and during pregnancy accounts for up to 90% of AIDS cases worldwide. This transmission is initiated by the passage of HIV across the mucosal barrier of sexual organs or placenta when exposed to infectious body fluids such as semen, vaginal secretions, or blood. The remaining AIDS cases are due to the transfusion of HIV-contaminated blood, needle sharing among intravenous drug users, accidental exposure to HIV-contaminated body fluids during invasive procedures, and other situations wherein infectious virus can come into direct contact with susceptible human tissues.

The currently available drugs for treating HIV infection and AIDS are not satisfactory. Toxicity or undesirable side effects of the common drugs for treating HIV infection, e.g., AZT or HIV protease inhibitors, are incompatible with their antiviral activity when used at an effective pharmaceutical concentration. Thus, there is still a need in the art for better alternative compounds for preventing and treating AIDS and HIV infection. The instant invention addresses this and other needs.

SUMMARY OF THE INVENTION

In one aspect, the present invention provides methods for identifying agents that inhibit HIV infection. The methods entail assaying a biological activity of an isopeptidase T (IsoT) molecule in the presence of test compounds to identify compounds that inhibit the biological activity of the IsoT molecule. These methods can further include testing the identified compound for ability to inhibit HIV infection. In some methods, the assayed biological activity is the isopeptidase activity of the IsoT molecule or its binding to another molecule (e.g., ubiquitin or Vpr). It can also be the expression of a gene encoding the IsoT molecule. Typically, the IsoT molecule employed in the screening is derived from a mammalian cell. In some preferred embodiments, a human IsoT molecule is employed.

In some of these screening methods, the ability to inhibit HIV-1 infection by the identified compound is examined by comparing HIV replication in an engineered HIV permissive cell that has been treated with the compound with HIV replication in a control cell that has not been treated with the compound. In some of these methods, the HIV permissive cell employed is HeLa-T4-βGal HIV cell. In some methods, HIV replication is monitored via a p24 antigen ELISA assay or a reverse transcriptase activity assay.

In some other methods of the invention, the ability to inhibit HIV infection by the identified IsoT-modulating compound is examined by comparing pseudovirus production in a host cell treated with the compound with pseudovirus production in a control host cell that has not been treated with the compound. In some of these methods, the host cell employed is 293T HEK cell. In some methods, the host cell is transfected with pseudovirus plasmids which produce HIV pseudovirus in the cell.

In a related aspect, the invention provides methods for identifying agents that inhibit HIV infection. These methods involve first screening test compounds to identify IsoT-modulating compounds that down-regulate the IsoT isopeptidase activity or its binding to Vpr, and then testing the identified IsoT-modulating compounds for ability to inhibit HIV infection. Typically, the IsoT molecule employed in the screening is derived from a mammalian cell. In some preferable embodiments, the IsoT molecule used in the screening is human IsoT.

In some of these methods, the ability to inhibit HIV-1 infection by an IsoT-modulating compound is examined by comparing HIV replication in an HIV permissive cell that has been treated with the compound with HIV replication in a control cell that has not been treated with the compound. In some methods, the HIV permissive cell employed is HeLa-T4-βGal HIV cell. In some of the screening methods, HIV replication is monitored via a p24 antigen ELISA assay or a reverse transcriptase activity assay.

In some other methods, the ability to inhibit HIV infection by the IsoT-modulating compound is examined by comparing pseudovirus production in a host cell treated with the compound with pseudovirus production in a control host cell that has not been treated with the compound. In some of these methods, the host cell employed is 293T HEK cell. In some methods, the host cell is transfected with pseudovirus plasmids which produce HIV pseudovirus in the cell.

In another aspect, the invention provides methods for treating HIV infection in a subject. Such methods entail administering to the subject suffering from HIV infection a pharmaceutical composition that contains an effective amount of an IsoT-modulating compound. The IsoT-modulating compound is able to down-regulate IsoT isopeptidase activity, IsoT binding to Vpr, or expression of an IsoT-encoding gene. In some of the methods, the IsoT-modulating compound employed is able to down-regulate human IsoT. In some methods, the IsoT-modulating compound employed is able to inhibit HIV replication in an IsoT-expressing cell in vitro. In some of these therapeutic methods, the IsoT-modulating compound is administered to the subject concurrently with a known anti-HIV drug. In some methods, the IsoT-inhibiting agent is a compound that has been identified by the present inventors that specifically inhibits IsoT activity. In some other methods, the IsoT-inhibiting agent is a nucleic acid molecule which specifically down-regulate expression or cellular level of IsoT, e.g., siRNAs or anti-sense DNAs.

A further understanding of the nature and advantages of the present invention may be realized by reference to the remaining portions of the specification and claims.

DETAILED DESCRIPTION

I. Overview

The invention is predicated in part on the discovery by the present inventors that IsoT is involved in HIV infection. Human IsoT is a 93 kDa zinc-binding deubiquitinating enzyme that is involved in the disassembly of free K48-linked polyubiquitin chains into ubiquitin monomers. The present inventors discovered that IsoT is a binding partner of viral protein R (Vpr) of the HIV-1 virus. Vpr is a 96-amino acid, 14 kDa accessory protein which is essential for HIV virus replication in monocytes and macrophages, and increases viral replication in T cells and T cell lines (see, e.g., Cohen et al., J Virol 64:3097-3099, 1990; Paxton et al., J Virol 67:7229-7237, 1993; and Andersen et al., Curr HIV Res. 3:43-51, 2005). The present inventors also found that over-expression of a wild-type IsoT, but not an active site mutant, increases virus titer from producer cells. In addition, it was observed that depletion of IsoT levels using small interfering RNAs reduces virus titer in HEK293T producer cells, and reduces the infectivity of laboratory strains HIV-1 (IIIb) and HIV-1 BaL in HeLa-T4-βGal and U373 HIV-1 indicator cell lines, respectively. These data indicate that IsoT plays an important role in increasing the efficiency of HIV-1 egress from the host cell.

In accordance with these discoveries, the present invention provides methods for screening novel agents that inhibit HIV infection. Test compounds are first screened for ability to modulate a biological activity of an IsoT molecule, e.g., its expression, its interaction with Vpr, or its isopeptidase activity. The agents thus identified are then typically further tested for ability to modulate HIV infection or an activity indicating HIV infection. Various IsoT molecules can be employed in the screening assays. For example, IsoT from human, rabbit, rat or mouse can be used to screen for the modulators. In some preferred embodiments, a human IsoT molecule is used. To exemplify utility of the screening methods disclosed herein, the present inventors performed a high throughput screening of small molecule compounds for inhibitors of human IsoT. As detailed in the Examples below, compounds with antiviral activities through inhibiting IsoT were identified from the screening.

The present invention also has therapeutic applications. Pharmacological inhibition of IsoT activities provides a novel approach for treating or preventing conditions related to HIV infection. Typically, the approach entails administering to a subject an IsoT inhibitor (e.g., an siRNA or a small molecule organic compound) that can be identified in accordance with the present invention.

The following sections provide guidance for making and using the compositions of the invention, and for carrying out the methods of the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Oxford Dictionary of Biochemistry and Molecular Biology*, Smith et al. (eds.), Oxford University Press (revised ed., 2000); *Dictionary of Microbiology and Molecular Biology*, Singleton et al. (Eds.), John Wiley & Sons (3$^{rd}$ ed., 2002); and *A Dictionary of Biology* (*Oxford Paperback Reference*), Martin and Hine (Eds.), Oxford University Press (4$^{th}$ ed., 2000). In addition, the following definitions are provided to assist the reader in the practice of the invention.

The term "test agent" or "test compound" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

HIV refers to human immunodeficiency virus (HIV) family of retroviruses. These viruses includes, but not limited to, HIV-I, HIV-II, HIV-III (also known as HTLV-II, LAV-1, LAV-2), and the like. As used herein, HIV can be any strains, forms, subtypes and variations in the HIV family.

The terms "identical" or "sequence identity" in the context of two nucleic acid sequences or amino acid sequences refers to the residues in the two sequences which are the same when aligned for maximum correspondence over a specified comparison window. Methods of alignment of sequences for comparison are well known in the art. Optimal alignment of sequences for comparison may be conducted by the local homology algorithm of Smith and Waterman (1981) Adv. Appl. Math. 2:482; by the alignment algorithm of Needleman and Wunsch (1970) J. Mol. Biol. 48:443; by the search for similarity method of Pearson and Lipman (1988) Proc. Nat. Acad. Sci U.S.A. 85:2444; by computerized implementations of these algorithms (including, but not limited to CLUSTAL in the PC/Gene program by Intelligentics, Mountain View, Calif.; and GAP, BESTFIT, BLAST, FASTA, or TFASTA in the Wisconsin Genetics Software Package, Genetics Computer Group (GCG), 575 Science Dr., Madison, Wis., U.S.A.). Alignment is also often performed by inspection and manual alignment.

The terms "substantially identical" nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (e.g., BLAST) using standard parameters. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The term "modulate" with respect to biological activities of an IsoT molecule refers to a change in the cellular level, subcellular localization or other biological activities of IsoT (e.g., its isopeptidase activity). Modulation of IsoT activities can be up-regulation (i.e., activation or stimulation) or down-regulation (i.e. inhibition or suppression). For example, modulation may cause a change in cellular level or enzymatic modification (e.g., phosphorylation) of IsoT, binding characteristics (e.g., binding to Vpr or a substrate), or any other biological, functional, or immunological properties of IsoT proteins. The change in activity can arise from, for example, an increase or decrease in expression of an IsoT-encoding gene, the stability of mRNA that encodes the IsoT protein, translation efficiency, or from a change in other bioactivities of the IsoT enzymes (e.g., its isopeptidase activity). The mode of action of an IsoT modulator can be direct, e.g., through binding to the IsoT protein or to a gene encoding the IsoT protein. The change can also be indirect, e.g., through binding to and/or modifying (e.g., enzymatically) another molecule which otherwise modulates IsoT.

The term "subject" refers to mammals, particularly humans. It encompasses other non-human animals such as cows, horses, sheep, pigs, cats, dogs, mice, rats, rabbits, guinea pigs, monkeys.

A "variant" of a molecule such as an IsoT is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

III. Screening Scheme

According to the present invention, novel inhibitors of HIV infection are identified by first screening test compounds for ability to modulate (e.g., inhibit) a biological activity of IsoT. The biological activity of IsoT to be monitored in the screening assays can be its isopeptidase activity. It can be its binding to another molecule, e.g., Vpr or ubiquitin. The biological activity can also be IsoT expression or its cellular level. After test compounds that modulate a biological activity of IsoT have been identified, they are typically further examined for ability to modulate HIV infection or to modulate an activity that is indicative of HIV infection or HIV replication. This step serves to confirm that by modulating the biological activity of IsoT, compounds identified in the first step can indeed regulate (e.g., inhibit) HIV infection.

Various biochemical and molecular biology techniques or assays well known in the art can be employed to screen for IsoT modulators. Such techniques are described in, e.g., *Handbook of Drug Screening*, Seethala et al. (eds.), Marcel Dekker ($1^{st}$ ed., 2001); *High Throughput Screening: Methods and Protocols (Methods in Molecular Biology,* 190), Janzen (ed.), Humana Press ($1^{st}$ ed., 2002); *Current Protocols in Immunology*, Coligan et al. (Ed.), John Wiley & Sons Inc (2002); Sambrook et al., *Molecular Cloning: A Laboratory Manual*, Cold Spring Harbor Press ($3^{rd}$ ed., 2001); and Brent et al., *Current Protocols in Molecular Biology*, John Wiley & Sons, Inc. (ringbou ed., 2003).

IsoT from various species can be employed in screening the IsoT modulators of the present invention. Preferably, a mammalian cell-derived IsoT molecule is employed. For example, human IsoT (Accession Nos. NM_003481 and NP_003472) was cloned and described in the art, e.g., Falquet et al., FEBS Lett. 376: 233-237; 1995; Wilkinson et al., Biochemistry 34:14535-14546, 1995; and Lacombe et al., FEBS Lett. 531:469-474, 2002. Other examples include chimpanzee IsoT (Accession Nos. XM_526393 and XP_526393) and mouse IsoT (Accession No. BC066993 and AAH66993). Any of these IsoT sequences or substantially identical sequences thereof can be employed in the screening assay to identify IsoT modulators in the present invention. As exemplified in the Examples below, cloning and expression of IsoT polynucleotides, as well as purification of IsoT polypeptides, can be performed with routinely practiced methods and techniques. Such methods and techniques are described in, e.g., Sambrook et al., supra; and Brent et al., supra. Specific methods for obtaining IsoT are also provided in the art, e.g., Gabriel et al., Biochemistry 41:13755-13766, 2002.

In addition to an intact IsoT molecule or nucleic acid encoding the intact IsoT molecule, an IsoT fragment (e.g., the catalytic domain or Vpr-binding domain), analog, or a functional derivative can also be used. The IsoT fragments that can be employed in these assays usually retain one or more of the biological activities of the IsoT molecule (e.g., its isopeptidase activity or binding to Vpr). As noted above, IsoTs from the different species have already been sequenced and well characterized. Therefore, their fragments, analogs, derivatives, or fusion proteins can be easily obtained using methods well known in the art. For example, a functional derivative of an IsoT can be prepared from a naturally occurring or recombinantly expressed protein by proteolytic cleavage followed by conventional purification procedures known to those skilled in the art. Alternatively, the functional derivative can be produced by recombinant DNA technology by expressing only fragments of an IsoT that retain its isopeptidase activity.

IV. Test Compounds

Test compounds that can be screened with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test compounds are synthetic molecules while others are natural molecules.

Test compounds are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test compounds can be naturally occurring proteins or their fragments. Such test compounds can be obtained from a natural source, e.g., a cell or tissue lysate. Libraries of polypeptide agents can also be prepared, e.g., from a cDNA library commercially available or generated with routine methods. The test compounds can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test compounds are polypeptides or proteins.

The test compounds can also be nucleic acids. Nucleic acid test compounds can be naturally occurring nucleic acids, random nucleic acids, or "biased" random nucleic acids. For example, digests of prokaryotic or eukaryotic genomes can be similarly used as described above for proteins.

In some preferred methods, the test compounds are small molecules, e.g., molecules with a molecular weight of not more than about 500 or 1,000. Preferably, high throughput assays are adapted and used to screen for such small molecules. In some methods, combinatorial libraries of small molecule test compounds as described above can be readily employed to screen for small molecule modulators of IsoTs. A number of assays are available for such screening, e.g., as described in Schultz et al., Bioorg Med Chem Lett 8:2409-2414, 1998; Weller et al., Mol Divers. 3:61-70, 1997; Fernandes et al., Curr Opin Chem Biol 2:597-603, 1998; and Sittampalam et al., Curr Opin Chem Biol 1:384-91,1997.

Libraries of test compounds to be screened with the claimed methods can also be generated based on structural studies of the IsoT polypeptides, their fragments or analogs. Such structural studies allow the identification of test compounds that are more likely to bind to the IsoT polypeptides. The three-dimensional structure of an IsoT polypeptide can be studied in a number of ways, e.g., crystal structure and molecular modeling. Methods of studying protein structures using x-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Computer modeling of an IsoT polypeptide structure provides another means for designing test compounds for screening IsoT modulators. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., *Physical Chemistry*, 4th Ed. Moore, W. J. (Prentice-Hall, New Jersey 1972), and *NMR of Proteins and Nucleic Acids*, K. Wuthrich (Wiley-Interscience, New York 1986).

Modulators of the present invention can also include antibodies that specifically bind to an IsoT polypeptide. Such antibodies can be monoclonal or polyclonal. Such antibodies can be generated using methods well known in the art. For example, the production of non-human monoclonal antibodies, e.g., murine or rat, can be accomplished by, for example, immunizing the animal with an IsoT polypeptide or its fragment (See Harlow & Lane, *Antibodies, A Laboratory Manual*, Cold Spring Harbor Laboratory Press, New York, 1988). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to an IsoT polypeptide of the present invention.

Human antibodies against an IsoT polypeptide can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using an IsoT polypeptide or its fragment.

V. Screen Test Compounds for IsoT Modulators

To identify novel compounds that inhibit HIV infection, test compounds are first screened for ability to modulate a biological activity of IsoT as described herein. In some preferred embodiments, test compounds are examined for ability to modulate (e.g., inhibit) the isopeptidase activity of IsoT. Compounds which modulate (e.g., inhibit) the enzymatic activity of IsoT can be identified with a number of assay formats. For example, as demonstrated in the Examples below, the screen can employ a biochemical assay using purified IsoT enzyme and ubiquitin-7-amido-4-methlcoumarin (Ub-AMC) as substrate. Effect of test compounds on the isopeptidase activity of IsoT can also be monitored using IsoT activity assays known in the art, e.g., Lacombe et al., FEBS Lett. 20:531:469-74, 2002; and Gabriel et al., Biochemistry. 19:41:13755-66, 2002. For example, the enzymatic activity of IsoT can be assayed with ubiquitin dimer substrates. Cleavage of the substrates by IsoT can be analyzed by electrophoresis and coomassie staining as described in Lacombe et al., FEBS Lett. 20:531:469-74, 2002. Branched and linear ubiquitin dimer substrates can be prepared as described in the art, e.g., Gabriel et al., Biochemistry 41:13755-13766, 2002. Other than ubiquitin dimers, other substrates can also be used to screen for modulators of IsoT enzyme activity. For example, a number of aminomethylcoumarin (AMC) based peptide substrates can be used to monitor IsoT activity (Stein et al., Biochemistry 34:12616-12623, 1995). These substrates (e.g., Z-Leu-Arg-Gly-Gly-AMC or ubiquitin-aldehyde) have been used in the art to study the kinetics of IsoT isopeptidase activity and inhibition of IsoT activity by ubiquitin aldehyde (Stein et al., Biochemistry 34:12616-12623, 1995; and Melandri et al., Biochemistry 35: 12893-12900, 1996).

In some other embodiments, test compounds can be first screened for an activity in modulating IsoT binding to another molecule such as Vpr or ubiquitin. Vpr can be cloned and expressed using methods described in the Examples below and also methods known in the art, e.g., Amini et al., J Biol. Chem. 279:46046-56, 2004; Iijima et al., Virol. 327:249-61, 2004; Yao et al., Retrovirology. 1:21-31, 2004; and Muthumani et al., Int Immunol. 17:103-16, 2005. Many assays and methods are available that can be used to examine the effect of test compounds on the binding of an IsoT polypeptide to Vpr or to ubiquitin. These include the methods generally known in the art for studying interactions between proteins and other compounds (including other proteins), e.g., labeled in vitro protein-protein binding assays, immunoprecipitation, GST pull-down assays, yeast or mammalian two-hybrid screens, and fluorescence quenching or fluorescence polarization. In addition, specific methods for examining IsoT binding with another molecule (e.g., ubiquitin) are also provided in the Examples below and in the art (see, Amini et al., J. Biol. Chem., 279:46046-46056, 2004; and Yao et al., Retrovirology. 1:21-31, 2004).

In some embodiments, the physical interaction between IsoT and Vpr binding can be analyzed by coimmunoprecitation as exemplified in the Examples below. Labeled or molecular tagged IsoT (e.g., FLAG-IsoT) and Vpr (e.g., Myc-Vpr) can be co-expressed in a host cell, e.g., 293T cells. IsoT binding with Vpr is examined by immunoprecitation of the cell lysate with an anti-FLAG antibody and followed by western blot analysis. Similarly, IsoT binding with ubiquitin can also be analyzed with methods known in the art. For example, IsoT-ubiquitin binding can be examined using an ubiquitin-Sepharose column submitted to a tandem KCl and urea linear gradients. This method was described in Lacombe et al. (FEBS Lett. 20:531:469-74, 2002) and Gabriel et al. (Biochemistry 41:13755-13766, 2002).

In some other methods, test compounds are assayed for activity to modulate expression or cellular level of IsoT, e.g., transcription, translation, or post-translational modification. Various biochemical and molecular biology techniques well known in the art can be employed to examine expression of an isoT gene or cellular levels of an IsoT polypeptide. Such techniques are described in, e.g., Sambrook et al., supra; and Brent et al., supra. In some embodiments, endogenous levels of an IsoT molecule can be directly monitored in cells normally expressing IsoT. In some embodiments, expression or cellular level of an IsoT molecule can be examined in an expression system using cloned cDNA or genomic sequence encoding the IsoT.

Alternatively, modulation of expression of an isoT gene can be examined in a cell-based system by transient or stable transfection of an expression vector into cultured cell lines. Assay vectors bearing transcription regulatory sequences (e.g., promoter) of an IsoT gene operably linked to reporter genes can be transfected into any mammalian host cell line for assays of promoter activity. Constructs containing an IsoT gene (or a transcription regulatory element of an IsoT gene) operably linked to a reporter gene can be prepared using only routinely practiced techniques and methods of molecular biology (see, e.g., Sambrook et al. and Brent et al., supra). General methods of cell culture, transfection, and reporter gene assay have been described in the art, e.g., Brent et al., supra; and Transfection Guide, Promega Corporation, Madison, Wis. (1998). Any readily transfectable mammalian cell line may be used to assay IsoT promoter function or to express IsoT, e.g., CHO, COS, HCT116, HEK293, MCF-7, and HepG2 are all suitable cell lines.

When inserted into the appropriate host cell, the transcription regulatory elements in the expression vector induces transcription of the reporter gene by host RNA polymerases. Reporter genes typically encode polypeptides with an easily assayed enzymatic activity that is naturally absent from the host cell. Typical reporter polypeptides for eukaryotic promoters include, e.g., chloramphenicol acetyltransferase (CAT), firefly or *Renilla* luciferase, beta-galactosidase, beta-glucuronidase, alkaline phosphatase, and green fluorescent protein (GFP).

In general, an IsoT-modulating compound identified in the screening is able to significantly alter a biological activity of IsoT (e.g., its isopepdidase activity or binding to Vpr). The extent of modulation is measured relative to the activity of the same compound on a control protein (e.g., luciferase or a protein kinase) or to the activity of a control compound on the same IsoT molecule. For example, an IsoT-modulating compound that inhibits IsoT expression or IsoT isopeptidase activity typically has an $IC_{50}$ (effective concentration that 
causes 50% of the maximum inhibition) for an IsoT molecule (e.g., human IsoT) that is at least 2, 5, 10, 25, 50, 100, 500, or 1000 fold lower than its $IC_{50}$ for a control enzyme. It can also be defined as having an $IC_{50}$ for IsoT that is at least 5, 10, 25, 50, 100, 500, or 1000 fold lower than the $IC_{50}$ of a negative control compound in inhibiting the same activity of the IsoT molecule. Similarly, if modulation is measured by inhibition of IsoT binding to Vpr, the presence of an IsoT-modulating compound usually can prevent or disrupt an IsoT-Vpr binding activity at a concentration that is at least 5, 10, 25, 50, or 100 fold lower than that a control compound in order to achieve the same extent of inhibition. As used herein, inhibition of IsoT binding to another molecule (e.g., Vpr or an ubiquitin multimer) means that binding affinity of IsoT to that molecule is decreased by at least 2 fold, preferably at least 5 fold, and more preferably, at least 10, 20, 50, or 100 fold.

VI. Screen for HIV-Inhibiting Compounds

To identify novel inhibitors of HIV infection, IsoT modulators described above are typically further tested to confirm their inhibitory effect on HIV infection. Typically, the compounds are screened for ability to modulate an activity that is indicative of HIV infection or HIV replication. Many assays and methods are available to examine HIV-inhibiting activity of the IsoT-modulating compounds. In some methods, potential inhibitory activity of IsoT-modulating compounds on HIV infection can be tested by examining their effect on HIV infection of a cultured cell in vitro, using methods routinely practiced in the art. For example, as exemplified in the Examples below, antiviral activity of the compounds can be assessed by monitoring viral replication in HeLaCD4βgal cells that have been contacted with the compounds prior to infection with an HIV virus. The compounds can also be tested on HIV infection of a primary macrophage culture as described in Seddiki et al., AIDS Res Hum Retroviruses. 15:381-90, 1999. They can also be examined on HIV infection of other T cell and monocyte cell lines as reported in Fujii et al., J Vet Med Sci. 66:115-21, 2004. Additional in vitro systems for monitoring HIV infection have been described in the art. See, e.g., Li et al., Pediatr Res. 54:282-8, 2003; Steinberg et al., Virol. 193:524-7, 1993; Hansen et al., Antiviral Res. 16:233-42, 1991; and Piedimonte et al., AIDS Res Hum Retroviruses. 6:251-60, 1990.

In these assays, HIV infection of the cells can be monitored morphologically, e.g., by a microscopic cytopathic effect assay (see, e.g., Fujii et al., J Vet Med Sci. 66:115-21, 2004). It can also be assessed enzymatically, e.g., by assaying HIV reverse transcriptase (RT) activity in the supernatant of the cell culture. Such assays are described in the art, e.g., Reynolds et al., Proc Natl Acad Sci USA. 100:1615-20, 2003; and Li et al., Pediatr Res. 54:282-8, 2003. Other assays monitor HIV infection by quantifying accumulation of viral nucleic acids or viral antigens. For example, Winters et al. (PCR Methods Appl. 1:257-62, 1992) described a method which assays HIV gag RNA and DNA from HIV infected cell cultures. Vanitharani et al. described an HIV infection assay which measures production of viral p24 antigen (Virology 289:334-42, 2001). Viral replication can also be monitored in vitro by a p24 antigen ELISA assay, as described in, e.g., Chargelegue et al., J Virol Methods. 38(3):323-32, 1992; and Klein et al., J Virol Methods. 107(2):169-75, 2003. All these assays can be employed and modified to assess anti-HIV activity of the IsoT-modulating compounds of the present invention.

In some methods, potential inhibiting effect of IsoT-modulating compounds on HIV infection can be examined in engineered reporter cells which are permissive for HIV replication. In these cells, HIV infection and replication is monitored by examining expression of a reporter gene under the control of an HIV transcription regulatory element, e.g., HIV-LTR. One example of such cells is HeLa-T4-βGal HIV reporter cell. As illustrated in Examples below, the HeLa-T4-βGal reporter cell can be infected with HIV-IIIb after being treated with an IsoT-modulating compound. Virus infectivity from the compound treated cells, as monitored by measuring β-galactosidase activity, can be compared with that from control cells that have not been treated with the compound. A reduced virus titer or reduction in infectivity from cells treated with the IsoT-modulating compound would confirm that the compound can indeed inhibit HIV infection or viral replication.

In addition to the Hela-T4-βGal cells exemplified herein, many similar reporter assays have also been described in the art. For example, Gervaix et al. (Proc Natl Acad Sci USA. 94:4653-8, 1997) developed a stable T-cell line expressing a plasmid encoding a humanized green fluorescent protein (GFP) under the control of an HIV-I LTR promoter. Upon infection with HIV-I, a 100- to 1,000-fold increase of fluorescence of infected cells can be observed as compared with uninfected cells. Any of these assay systems can be employed in the present invention to monitor effects of the IsoT-modulating compounds on HIV infection in real time. These in vitro systems also allow quantitation of infected cells over time and determination of susceptibility to the compounds.

In some other methods, effect of the IsoT-modulating compounds on HIV replication can be examined by examining production of HIV-1 pseudovirus in a cell treated with the compounds. The cell can express IsoT endogenously or exogenously. An IsoT-encoding construct can also be transfected into the host cell, especially for host cells that do not express IsoT endogenously. As described in the Examples below, production of HIV-1 pseudovirus can be obtained by transfecting a producer cell (e.g., a 293T HEK cell) with a reporter plasmid expressing the psi-positive RNA encoding a reporter gene (e.g., luciferase gene), a delta psi packaging construct encoding all structural proteins and the regulatory or accessory proteins such as Tat, Rev, Vpr, and Vif, and a VSV-g envelop expression plasmid. The pseudovirus produced in the producer cell encodes only the reporter gene. After infecting a target cell with pseudovirus in the supernatant from the producer cell, the reporter gene is expressed following retrotranscription and integration into the target cell genome.

To screen for inhibitors of HIV replication, the producer host cell can be treated with an IsoT-modulating compound prior to, concurrently with, or subsequent to transfection of the pseudovirus plasmids. Preferably, the compound is administered to the host cell prior to transfection of the pseudovirus plasmids, and is present throughout the assay process. Titer of the produced pseudovirus can be monitored by infecting target cells with the pseudovirus in the supernatant from the producer cell and assaying an activity of the reporter (e.g., luciferase activity) in the target cells. As a control, reporter activity in target cells infected with supernatant from producer cells that have not been treated with the compound is also measured. If the IsoT-modulating compound has an inhibitory effect on virus budding, target cells contacted with the supernatant from the producer cells that have been treated with the compound will have a reduced reporter activity relative to the control cells.

VII. Therapeutic Applications

By down-regulating (i) IsoT isopeptidase activity; (ii) IsoT binding to Vpr, or (iii) expression of an IsoT-encoding gene, the IsoT-modulating compounds described above provide useful therapeutic applications for the present invention.

They can be readily employed to inhibit HIV replication in cells infected by HIV. They are also useful to prophylactically or therapeutically treat subjects suffering from HIV infections, as well as diseases or conditions associated with HIV infections (e.g., AIDS). HIV infections that are amenable to treatment with the IsoT-modulating compounds of the invention encompass infection of a subject, particularly a human subject, by any of the HIV family of retroviruses (e.g., HIV-1 or HIV-2). The IsoT-modulating compounds are useful for treating a subject who is a carrier of any member of the HIV family of retroviruses. They can be used to treat a subject who is diagnosed with active AIDS. The compounds are also useful in the treatment or prophylaxis of the AIDS-related conditions in such subjects. Subjects who have not been diagnosed as having HIV infection but are believed to be at risk of infection by HIV are also amenable to treatment with the IsoT-modulating compounds of the present invention.

The IsoT-inhibiting compounds that can be employed in the therapeutic applications of the invention include small molecule organic compounds that can be identified in accordance with the methods of the present invention, as demonstrated in Examples below. Once identified, such compounds can be readily synthesized using routinely practiced methods of organic chemistry and/or can be readily obtained from commercially suppliers. The IsoT modulators that are suitable for practicing the therapeutic methods of the invention also include other compounds that can specifically modulate IsoT cellular level or its biological activities (e.g., its enzymatic activity). Such compounds include antagonist or agonist antibodies which specifically recognize an IsoT polypeptide. They also include nucleic acid modulators such as short interfering RNA (siRNA), microRNA (miRNA), and synthetic hairpin RNA (shRNA), anti-sense nucleic acid, or complementary DNA (cDNA). For example, the IsoT-specific or Vpr-specific siRNAs disclosed in the Examples below can be used. Additionally, the therapeutic applications can also employ other IsoT-inhibiting agents that can be identified in accordance with the above described screen methods.

Subjects suffering from any AIDS-related conditions may be suitable for treatment with the IsoT-modulating compounds of the present invention. Such conditions include AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as *Pneumocystis carinii* pneumonia, Mycobacterial tuberculosis, esophageal candidiasis, toxoplasmosis of the brain, CMV retinitis, HIV-related encephalopathy, HIV-related wasting syndrome, etc.

Standard methods for measuring in vivo HIV infection and progression to AIDS can be used to determine whether a subject is positively responding to treatment with the IsoT-modulating compounds of the invention. For example, after treatment with an IsoT-modulating compound of the invention, a subject's $CD4^+$ T cell count can be monitored or the subject's viral load. A rise in $CD4^+$ T cells indicates that the subject is benefiting from administration of the antiviral therapy. This, as well as other methods known to the art, may be used to determine the extent to which the compounds of the present invention are effective at treating HIV infection and AIDS in a subject.

The IsoT modulators of the present invention can be directly administered under sterile conditions to the subject to be treated. The modulators can be administered alone or as the active ingredient of a pharmaceutical composition. The therapeutic composition of the present invention can also be combined with or used in association with other therapeutic agents. In some applications, a first IsoT modulator is used in combination with a second IsoT modulator in order to inhibit HIV infection to a more extensive degree than cannot be achieved when one IsoT modulator is used individually. In some other applications, an IsoT-modulating compound of the present invention may be used in conjunction with known anti-HIV drugs such as AZT.

Pharmaceutical compositions of the present invention typically comprise at least one active ingredient together with one or more acceptable carriers thereof. Pharmaceutically acceptable carriers enhance or stabilize the composition, or facilitate preparation of the composition. Pharmaceutically acceptable carriers are determined in part by the particular composition being administered (e.g., nucleic acid, protein, or modulatory compounds), as well as by the particular method used to administer the composition. They should also be both pharmaceutically and physiologically acceptable in the sense of being compatible with the other ingredients and not injurious to the subject. This carrier may take a wide variety of forms depending on the form of preparation desired for administration, e.g., oral, sublingual, rectal, nasal, intravenous, or parenteral. For example, the IsoT-modulating compound can be complexed with carrier proteins such as ovalbumin or serum albumin prior to their administration in order to enhance stability or pharmacological properties.

The pharmaceutical compositions can be prepared in various forms, such as granules, tablets, pills, suppositories, capsules, and the like. The concentration of therapeutically active compound in the formulation may vary from about 0.1 to 100% by weight. Therapeutic formulations are prepared by any methods well known in the art of pharmacy. The therapeutic formulations can be delivered by any effective means which could be used for treatment. See, e.g., *Goodman & Gilman's The Pharmacological Bases of Therapeutics*, Hardman et al., eds., McGraw-Hill Professional ($10^{th}$ ed., 2001); *Remington: The Science and Practice of Pharmacy*, Gennaro (ed.), Lippincott Williams & Wilkins ($20^{th}$ ed., 2003); and *Pharmaceutical Dosage Forms and Drug Delivery Systems*, Ansel et al. (eds.), Lippincott Williams & Wilkins ($7^{th}$ ed., 1999).

The therapeutic formulations can be conveniently presented in unit dosage form and administered in a suitable therapeutic dose. A suitable therapeutic dose can be determined by any of the well known methods such as clinical studies on mammalian species to determine maximum tolerable dose and on normal human subjects to determine safe dosage. Except under certain circumstances when higher dosages may be required, the preferred dosage of an IsoT modulator usually lies within the range of from about 0.001 to about 1000 mg, more usually from about 0.01 to about 500 mg per day.

The preferred dosage and mode of administration of an IsoT modulator can vary for different subjects, depending upon factors that can be individually reviewed by the treating physician, such as the condition or conditions to be treated, the choice of composition to be administered, including the particular IsoT modulator, the age, weight, and response of the individual subject, the severity of the subject's symptoms, and the chosen route of administration. As a general rule, the quantity of an IsoT modulator administered is the smallest dosage which effectively and reliably prevents or minimizes the conditions of the subjects. Therefore, the above dosage ranges are intended to provide general guidance and support for the teachings herein, but are not intended to limit the scope of the invention.

EXAMPLES

The following examples are offered to illustrate, but not to limit the present invention.

Example 1

Vpr Interacts with the C-Terminal Region of IsoT

The Vpr-IsoT interaction was identified by a yeast two-hybrid screen using a human leukocyte library. Assays of protein-protein interaction in yeast were done with GAL4 and LexA fusion proteins. A human leukocyte cDNA library cloned into the GAL4 expression vector (Clontech) was screened using the HIV HXB2 Vpr as bait. Vpr cDNA was amplified by PCR using Vpr-specific primers. The cDNA was inserted into the LexA DBD expression vector pSLANS. pSLANS is a modified version of pBTM116 (Bartel et al Biotechniques 14: 920-924, 1993). It was modified to accept NotI inserts and to place gly-4-ser-gly-4-ser between LexA and the bait. The cDNA encoding the LexA DBD —Vpr fusion protein was transformed into the L40 MATa yeast strain. The cDNAs encoding the Gal4 AD—leukocyte cDNA fusion proteins were transformed into the yeast strain 540 MATα. The two yeast strains were mated and transformants containing both plasmids were selected in THUKL-deficient synthetic media, and protein interactions were analyzed by a galactosidase filter assay.

Figure 1:
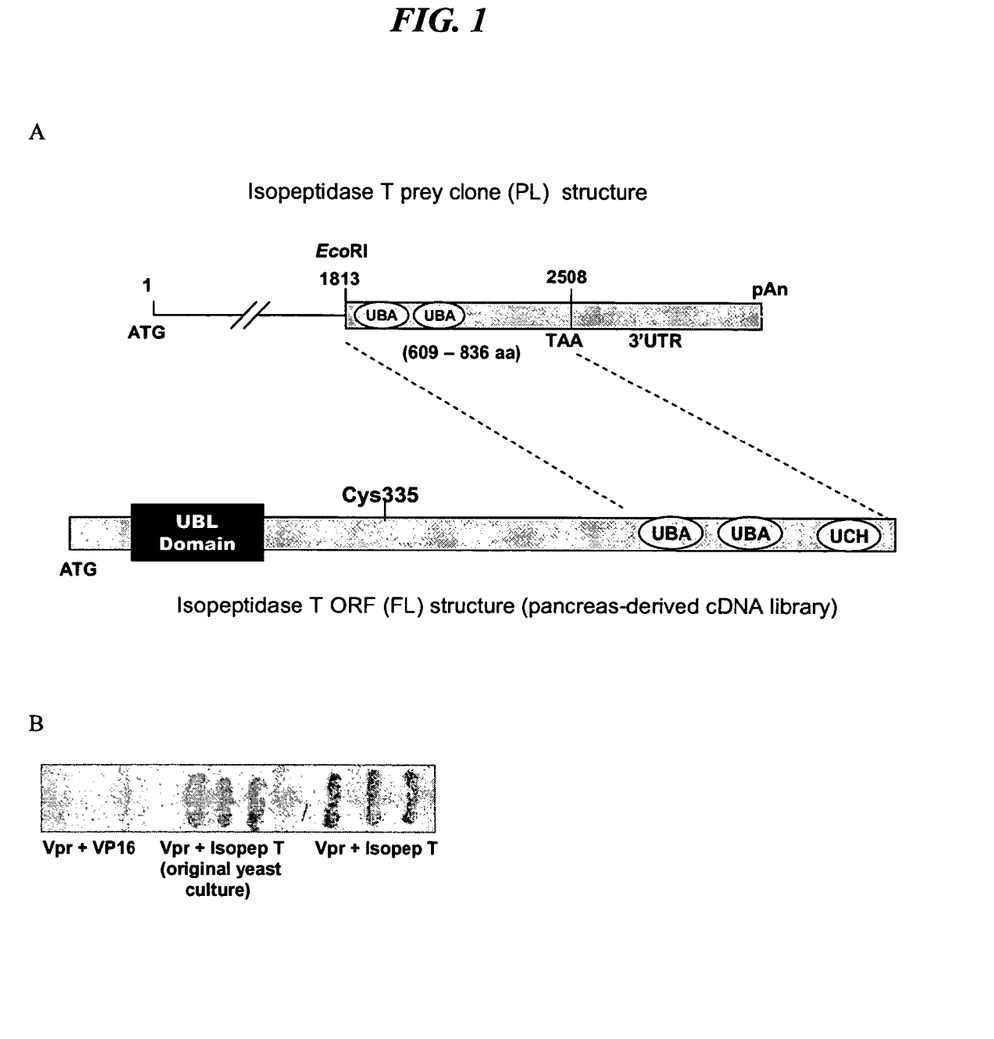
FIGS. 1A-1B show that Vpr binds to IsoT: (A) Schematic diagram and alignment of the IsoT prey clone identified by yeast-2-hybrid relative to the full-length IsoT cDNA. The prey clone contains the C-terminal 227 amino acids possessing the two UBA domains. The full-length IsoT cDNA clone used in this report was amplified from a pancreas-derived cDNA library. The relative position of C335, the active site cysteine, is indicated. (B) Yeast two-hybrid assays showing specific interactions between Vpr and IsoT using the β-galactosidase filter lift assay. VP16, an empty vector.

HIV-1 HXB2 Vpr was used as the bait in a yeast two-hybrid screen to identify novel interacting host cell factors encoded in a human leukocyte cDNA library. Approximately two million diploid transformants were screened and numerous positive candidates were isolated. Positive colonies were assayed for β-galactosidase activity using a filter lift assay for further confirmation of the protein-protein interaction. Sequencing of independent candidate cDNA clones and comparison to the GenBank database identified one interacting partner to be IsoT, a component of the 26S proteasome. IsoT is primarily responsible for the recycling of ubiquitin sequestered in free polyubiquitin chains. Sequence analysis of the prey-length (PL) IsoT confirmed the clone contained the C-terminal 227 amino acids and an additional 635-bp of the 3'-UTR (FIG. 1A). Interestingly, the PL clone possesses two UBA domains analogous to the hHR23A DNA damage repair enzyme previously identified to interact with Vpr through the UBA(2) domain. β-galactosidase activity confirmed the interaction of IsoT and Vpr in yeast, whereas Vpr and the negative control vector, VP16, showed no β-galactosidase activity (FIG. 1B). The Vpr protein derived from HXB2 is frameshifted by the insertion of a single T nucleotide leading to five frameshifted amino acids at positions 74 to 78. Thus, the C-terminal region of Vpr (amino acids positions 74 to 96) is not required to mediate binding to IsoT. These residues (84-94) appear to be important for virion incorporation (Paxton et al., 1993).

We also performed co-immunoprecipitation experiments to analyze Vpr-IsoT interactions in mammalian cells. An IsoT mammalian expression vector was constructed by fusing a FLAG epitope to the 5'-end of the full-length IsoT gene. The VIP3 vector was modified to express either a Myc tag (for Myc:Vpr fusion proteins) or with a FLAG tag (for FLAG: IsoT fusion proteins). A full-length clone of IsoT was obtained by PCR amplification of a pancreas-derived cDNA library using IsoT-specific primers and confirmed to be IsoT by sequence analysis prior to subcloning into the FLAG-tagged VIP3 vector. Approximately 3×10e6 293T cells (10 cm plate) were transfected with 20 μg of FLAG-IsoT and/or Myc-Vpr using CaP (Clontech). At 24 hr after transfection, cells were lysed for 30 min on ice in a gentle hypotonic buffer (0.5% triton-X, 20 mM Tris-HCl, 50 mM NaCl, 10% glycerol and protease inhibitor cocktail) [Complete, Roche Molecular Biochemicals]. Cell lysates were clarified by centrifugation at 16,000×g for 5 minutes (check), and the supernatants were immunoprecipitated (2 hr, 4° C.) with anti-FLAG antibody M2 (Sigma—check), and subsequently incubated with protein A conjugated gel beads. Bound proteins were eluted by boiling in SDS sample buffer and aliquots were analyzed by SDS-PAGE and western blotting with goat anti-Myc antibody.

The results demonstrated the interaction of Vpr and IsoT in human cells following over-expression of epitope-tagged IsoT and Vpr in HEK293T cells (data not shown).

Example 2

IsoT cDNA Over-Expression Increases HIV Production

In order to define a role of IsoT in the HIV life cycle, IsoT was transfected in parallel with the pseudovirus plasmids and the virus supernatant was analyzed by transducing target 293T cells and assaying for luciferase reporter activity. Transient transfection of 293T HEK cells for production of pseudovirus was performed using the calcium phosphate method (Clontech) in 6-well microtiter plates (3×105 cells/well). The luciferase vector plasmid (encodes genomic RNA), delta psi packaging construct (encodes all structural proteins, as well as the regulatory and accessory proteins Tat, Rev, Vpr, and Vif) and VSV-g envelop expression plasmid were transfected at a ratio of 2.0:1.5:0.5 (2, 1.5, 0.5ug DNA, respectively/well). Luciferase reporter activity was measured following transduction of 293T target cells with equivalent aliquots of virus supernatant in either 96-well or 384-well format using Bright-Glo luciferase substrate and an Acquest plate reader with the appropriate luminescence filter. Values are expressed in relative light units (RLU).

Figure 2:
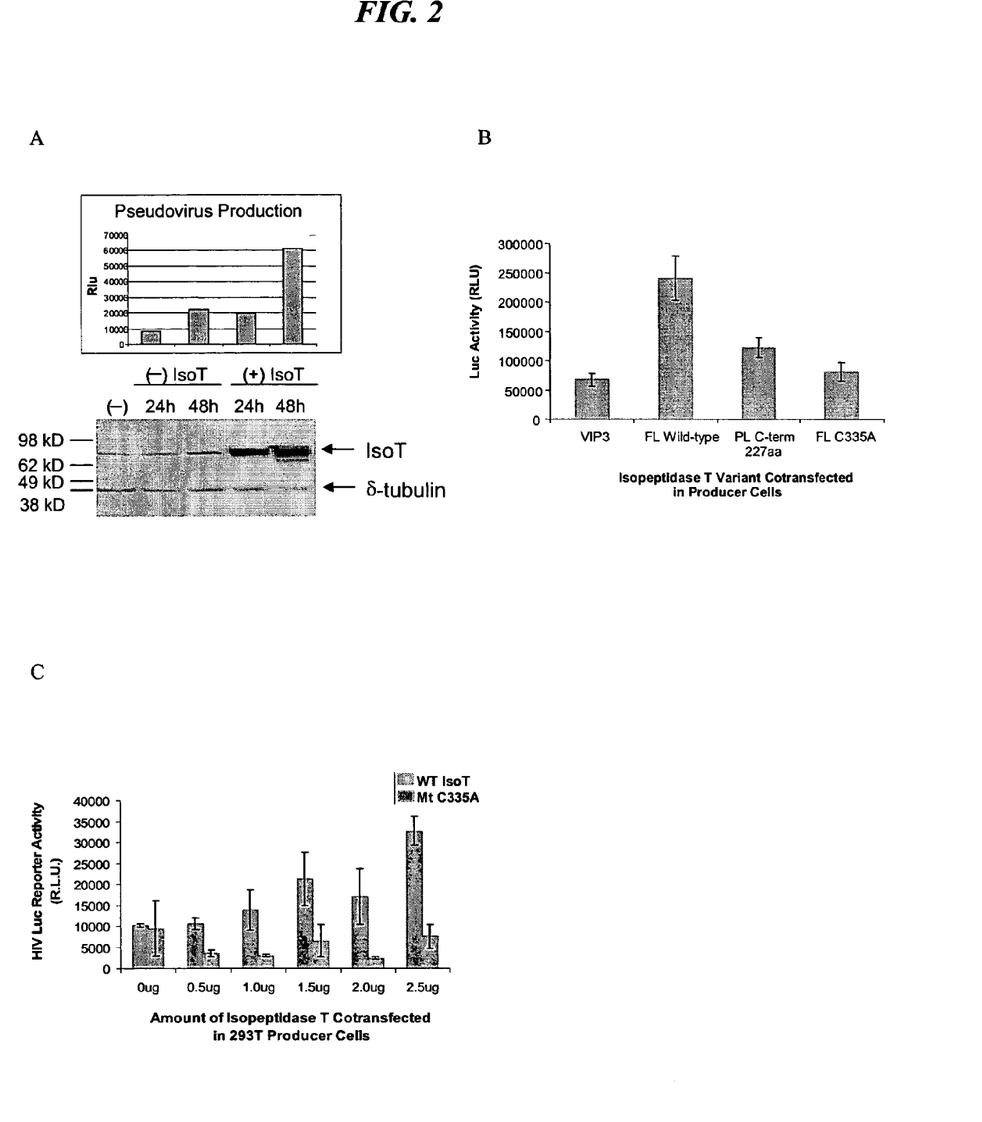
FIGS. 2A-2C show that wild-type IsoT over-expression increases HIV-1 virus titer while an active site mutant does not: (A) overexpression of full-length (FL) wild-type IsoT increases pseudovirus expression at 24 and 48 hours after transfection. 293T cells were cotransfected with three pseudovirus plasmids in the presence (+) or absence (−) of a fourth cDNA encoding IsoT. Reporter virus supernatant was collected at either 24 or 48 hours after transfection and assayed for reporter activity in 293T target cells. Cell lysates were analyzed in parallel by Western analysis using an IsoT-specific antibody for endogenous IsoT expression as well as over-expressed IsoT. Lane 1, no transfected plasmids, transfection reagent only. (B) 293T cells were cotransfected as in (A), with either VIP3 (plasmid backbone), FL-wild-type, PL-C-term 227, or FL-C335A as the fourth plasmid. Luciferase reporter activity from the virus supernatant collected 30 hours post-transfection was assayed in 293T target cells. (C) Dose-dependent IsoT functional effect on HIV titer. FL-WT and FL-C335A were titrated and transfected as the fourth plasmid in parallel with the pseudovirus plasmids.

The pseudovirus produced encodes only the luciferase gene that is expressed following retrotranscription and integration into the target cell genome. Enhanced or reduced effects on virus budding by cotransfection of a $4^{th}$ plasmid will be reflected by changes in luciferase activity on target cells relative to the pseudovirus plasmids alone. Virus supernatant collected at 24 hours post-transfection in the presence of overexpressed IsoT led to a two-fold (50%) increase in virus production (10,000 rlu vs. 20,000 rlu). At 48 hours post-transfection, virus production was increased three-fold in the presence of IsoT (FIG. 2A). Concomitant with the observed increases in pseudovirus infectivity after 24 and 48 hours of virus production, we show a parallel increase in exogenous IsoT expression by Western analysis (FIG. 2A).

To further evaluate the role of IsoT, a catalytically inactive mutant was generated that replaced the active site cysteine at residue 335 with alanine. The IsoT-C335A mutant was generated using site-directed nucleotide substitutions prepared by a PCR-based method for site-directed mutagenesis. PCR was performed with native Taq DNA polymerase under conditions specified by the manufacturer (Perkin-Elmer). The PCR product was engineered to possess appropriate restriction sites that facilitated the subcloning of the C335A fragment into the IsoT cDNA:VIP3 plasmid. The custom oligonucleotide primers were obtained commercially from NNN. The template for PCR was the IsoT:VIP3 construct.

Expression of the IsoT-C335A mutant was not expected to increase HIV pseudovirus production if inactive, and this is illustrated in FIG. 2B. Over-expression of the full length wildtype (FL-WT) IsoT increased titer by ~2.5-fold relative to the C335A mutant. The prey-length clone could not substitute for the phenotype observed with the full-length clone suggesting that a functionally active protein in the correct conformation was important for mediating the increase in virus titer. A dose-dependent effect of FL-WT IsoT expression on increasing HIV titer was observed as IsoT was titrated into producer cells in parallel with HIV-1 vector plasmids. Conversely, expression of the C335A appeared to act in a transdominant negative manner decreasing HIV titer by approximately fifty percent compared to levels observed with endogenously expressed IsoT only (FIG. 2C, 0 µg). Expression levels of FL and the C335A mutant proteins were comparable as determined by western analysis (data not shown).

Example 3

Blocking Vpr Incorporation Decreases Levels of Virus Production

Figure 3:
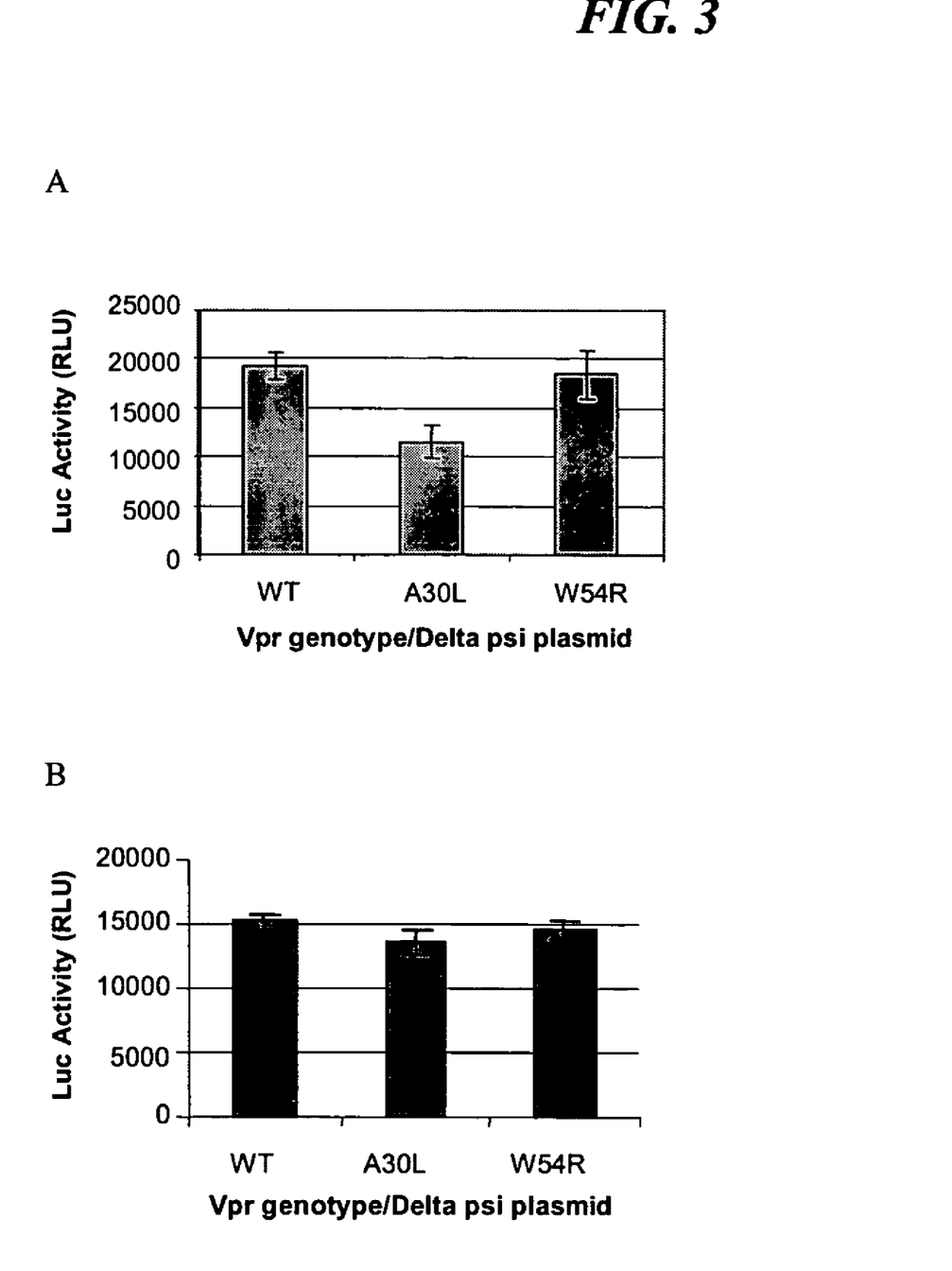
FIGS. 3A-3B show that decreased budding of Vpr (A30L) virus correlates with decreased particle production, but not infectivity. 293T cells were transfected with pseudovirus DNAs expressing WT and mutant versions of Vpr. (A) The A30L Vpr incorporation mutant, but not WT or the nuclear localization mutant W54R, decreased virus titer as measured by infectivity in 293T target cells. (B) p24 levels were normalized (9.38 ng) from (A) for pseudovirus input used to infect target 293T cells.

An HIV virion incorporation mutant of Vpr was generated by replacing the alanine with a lysine at codon 30 in Vpr in the background of the delta psi packaging plasmid. As anticipated, the Vpr-A30L virion incorporation mutant led to a 40% decrease in virus production relative to WT virus production as measured by the luciferase activity of the reporter virus in target 293T cells (FIG. 3A). In contrast, a mutant Vpr defective in nuclear localization (W54R) had no appreciable effect on virus production. p24 levels were also quantitated from aliquots of virus supernatants correlating the decrease in infectivity in FIG. 3A with an associated 40% decrease in the number of virus particles released from the producer cells (data not shown). The infectivity of the viruses produced was not affected by the mutations introduced into Vpr following normalization to p24 levels (FIG. 3B).

Example 4

Inhibition of HIV Particle Production by IsoT Depletion

With the observations that over-expression of IsoT led to increased virus vector production and blocking incorporation of Vpr led to a decrease in virus vector production, we next examined the effect of depleting levels of IsoT and Vpr on HIV-1 vector production. To validate siRNA efficacy for the IsoT and Vpr target mRNA, FLAG-tagged IsoT and Myc-tagged Vpr were over-expressed in 293Ts following introduction the day before of small interfering siRNAs targeting IsoT and Vpr RNA, respectively. Two siRNAs were designed each against IsoT, Vpr, and Tat and were ordered HPP grade from Qiagen. Specifically, the sequences of IsoT-specific siRNAs are: IsoT 1: 5'-AGUUCACCUUCGGCUUAGAUU-3' (SEQ ID NO:1); and IsoT 2: 5'-GGCAGAUGGGUGAUCUACA-dTdT-3' (SEQ ID NO:2). Sequences of Vpr-specific siRNAs are: Vpr 1: 5'-GGAGUGGAAGCCAUAAUAA-UU-3' (SEQ ID NO:3) and Vpr 2: 5'-ACAACUGCUGUUUAUC-CAUUU-3' (SEQ ID NO:4). Sequences of Tat-specific siRNAs are Tat 1: 5'-CUGCUUGUACCAAUUGCUA-dTdT-3' (SEQ ID NO:5); and Tat 2: 5'-GCCUUAGGCAUCUC-CUAUG-dTdT-3' (SEQ ID NO:6). The two siRNAs were combined at a 1:1 ratio and used as a pool in experiments unless otherwise noted. Other siRNAs used in the experiments were ordered from Dharmacon Research.

All siRNAs tested efficiently depleted levels of either IsoT or Vpr (data not shown), thereby validating the selected siRNAs. Upon production of a custom made IsoT antibody, the depletion of endogenous IsoT was confirmed. Higher depletion of endogenous levels was observed at 72 hr after siRNA treatment than at 48 hr. There was no effect on 293T cell viability as assessed by alamar blue (mitochondrial activity) and cell titer glo (ATP release) cell viability kit reagents (data not shown).

Figure 4:
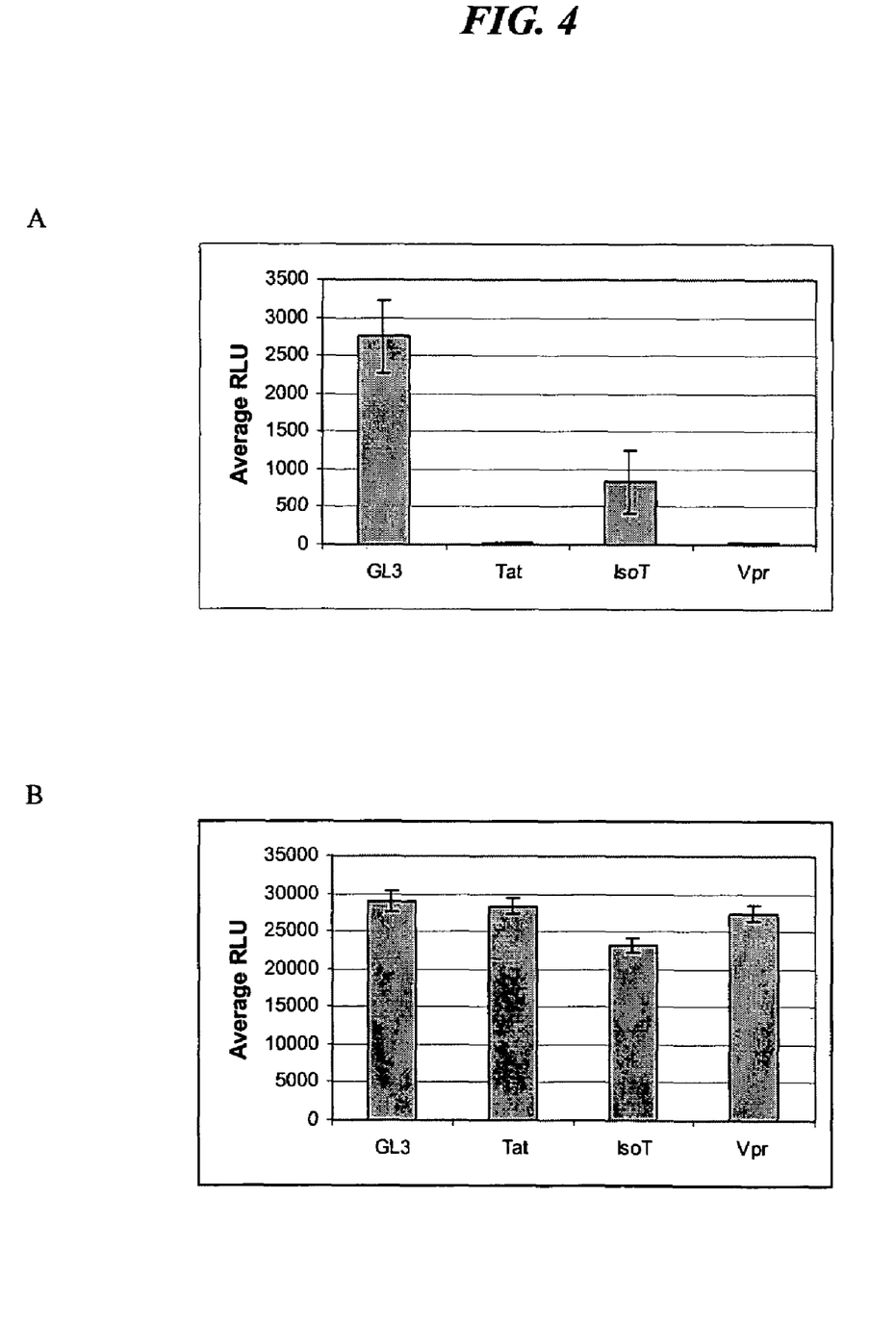
FIGS. 4A-4B show that depletion of IsoT or Vpr by RNA interference inhibits pseudovirus production in 293T cells. (A) 293T cells were transfected with the indicated siRNA targeting HIV Tat, IsoT, Vpr, or Luciferase GL3 (negative control). Cells were cultured overnight and subjected to cDNA transfection of the 3 plasmid pseudovirus system at a ratio of vector RNA:delta psi:env of 2:0.05:0.5 or 100 ng:2.5 ng:25 ng per well. Three replicate wells were run per condition. Virus supernatants were collected 48 hours later and used to infect target 293T cells. Luciferase activity in these transduced cells was determined 48 hours and is shown in A. (B) 293T cells were transfected with siRNAs against HIV Tat, IsoT, Vpr or Luciferase GL3. 72 hours later cell viability was determined using CellTiterGlo and measuring luminescence.

In order to assess the effect of IsoT depletion on virus vector production, 293T cells were treated with siRNAs and followed the next day with pseudovirus plasmid transfections and the virus was harvested two days later and infectivity gauged in 293T target cells. Depletion of IsoT and Vpr protein levels by RNA interference led to a reduction in titer assessed in 293T target cells (FIG. 4). IsoT depletion led to a reduction in titer (infectivity) by 60% (FIG. 4A). This was dependent on non-saturating conditions; virus output was in the linear range as regulated by the amount of delta psi (structural genes) transfected into the producer cells and/or the length of time prior to virus harvest (after 48 hr, virus output was typically saturated). Surprisingly, depletion of Vpr levels severely reduced virus production comparable to depleting Tat levels. Depleting levels of Vpr produced from the delta psi packaging plasmid under non-saturating conditions clearly is critical for infectious virus particle formation in this assay system. None of the siRNA used exhibited any appreciable toxicity in 293Ts (FIG. 4B).

The observation that Vpr and Tat depletion effectively blocked virus production, whereas IsoT depletion reduced infectious virus production by only 60%, may be due in large part to the addition of small interfering RNAs prior to de novo synthesis of Tat and Vpr. This is similar to the observed results with IsoT depletion of exogenous vs. endogenous IsoT. It is likely that IsoT protein synthesized prior to RNA interference may still be recruited by Vpr to enhance budding and release. Five independent and unique siRNAs targeting IsoT were shown to effectively decrease protein expression and HIV pseudovirus titer (data not shown).

Example 5

Depletion of IsoT and Vpr Levels Decreases HIV-1 IIIb Replication

Figure 5:
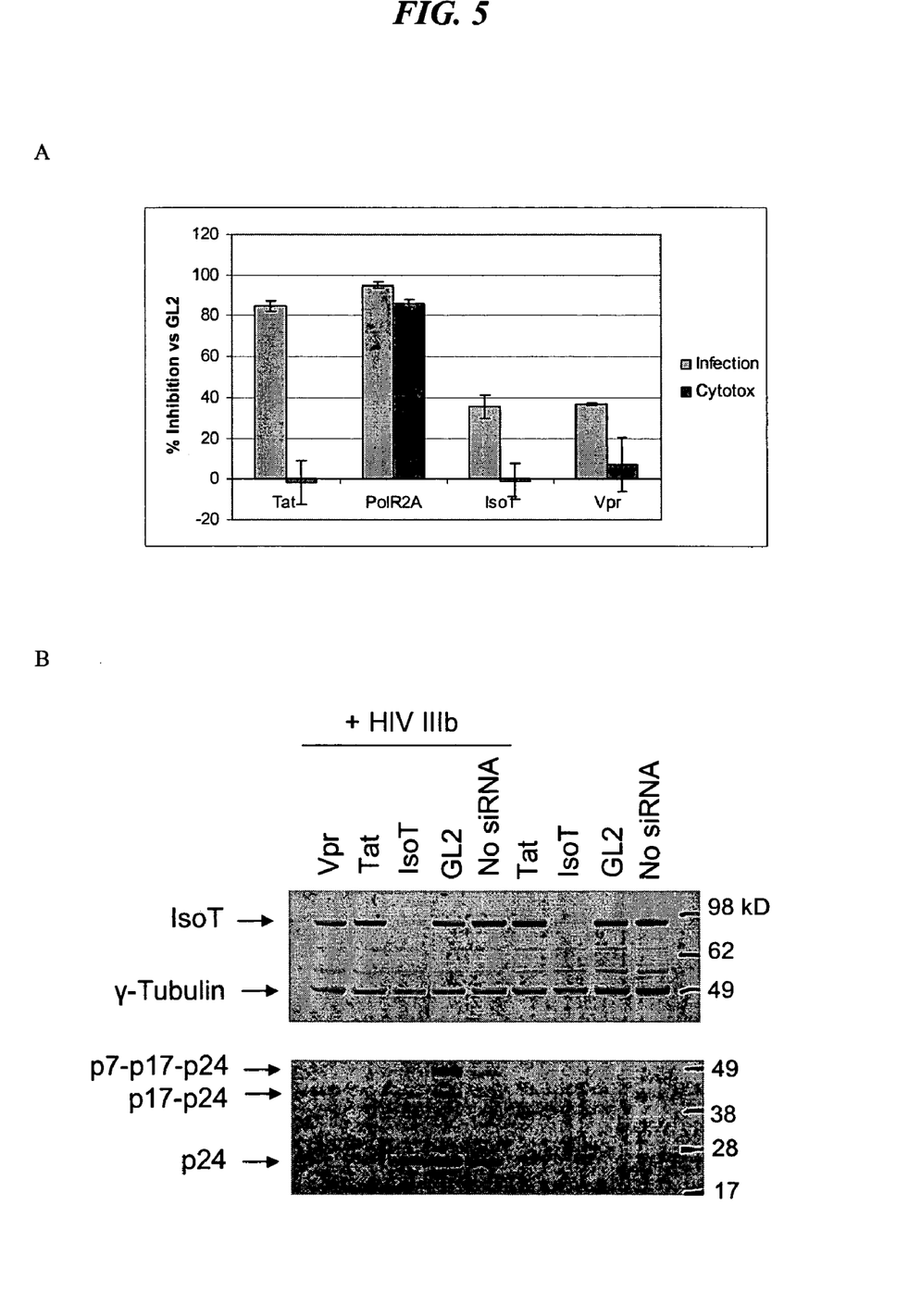
FIG. 5 shows that depletion of IsoT or Vpr inhibits HIV-1 IIIb replication in HeLa-CD4-β-gal cells. Cells were transfected with the indicated siRNAs targeting Tat, IsoT, Vpr, Luciferase GL2 (negative control), or PolR2A (positive control for cytotoxicity). After culturing 24 hours, the cells were infected with HIV-1 IIIb. β-galactosidase activity was determined 72 hours post-infection as a measure of infection. Cytotoxicity was determined in parallel on siRNA-transfected but uninfected cells. The data is expressed as a percentage of the signal generated by the negative control GL2 siRNA-transfected cells.

We next wanted to examine the effect of IsoT and Vpr depletion in cells permissive for HIV replication. To this end, HeLa-T4-βGal HIV reporter cells were infected with HIV IIIb following siRNA treatment. The HeLa-CD4-Bgal cells (Kimpton et al., J Virol 66:2232-2239, 1992) were obtained from Dr. Michael Emerman through the AIDS Research and Reference Reagent Program, Division of AIDS, NIAID, NIH. The results show that after a 72 hr infection, IsoT or Vpr depletion reduced HIV replication by almost 40% with no appreciable cytotoxicity observed (FIG. 5). Depletion of Tat levels reduced replication by ~85%. As a control for cellular toxicity through depletion of a host cell factor, RNA interference was used to diminish RNA Pol II levels. A marked decrease in cell viability in the presence of depleted RNA Pol II levels accounted fully for the observed inhibition of virus replication. These data are consistent with a role for IsoT and Vpr supporting efficient HIV-1 replication in permissive cells, a mechanism not attributable to cellular toxicity.

We also assessed the effects of diminished levels of IsoT in normal epithelial cells. To this end, IsoT levels were depleted in IOSE-80 cells using small interfering RNA. The results indicate that depletion of IsoT levels do not affect normal epithelial cell viability, whereas depletion of RNA Pol II levels reduced viability by 65% (data not shown). These results indicate that down-regulation of IsoT function may not affect the viability of normal, uninfected cells.

Example 6

Identifying HIV-Inhibiting Compounds with the Claimed Screening Methods

This Example describes identification of HIV inhibitors using the methods described above. Specifically, a library of small molecule organic compounds were screened in a high-throughput format. Test compounds were screened for ability to inhibit IsoT. Hit compounds identified from the primary screening were further examined for effect on inhibiting HIV infection. Briefly, a biochemical assay of IsoT enzymatic activity was developed, using ubiquitin-7-amido-4-methl-coumarin (Ub-AMC) as a substrate. The cleavage and liberation of AMC by IsoT generates a fluorescent signal with excitation at 380 nm and emission at 460 nm. Inhibition of the cleavage activity in the presence of a compound constitutes a screen hit. An in-house small molecule compound collection ($1.7 \times 10^6$ compounds) was screened in a 1536-well HTS format using IsoT enzyme generated in-house. The screen hit rate was 0.4%. The original hits (87.3% reconfirmed of 1,761 compounds available) were first subject to reconfirmation, removal of cytotoxic compounds, and assaying of purified compounds. The identified compounds were then examined for activity in inhibition of HIV replication, and other prioritization characteristics (e.g., potency, selectivity window, chemical tractability). There were a total of six compounds that were identified as potential HIV inhibitors.

A representative HIV-inhibiting compound thus identified is Compound A. The $IC_{50}$ of this compound for IsoT protease inhibition is 129 nM. The $EC_{50}$ of the compound for antiviral activity against HIV IIIb in the HeLa-T4-bGal infection model is 6.14 µM, with no cytotoxicity observed. When assayed against a deubiquitinating (DUB) enzyme panel, the compound was found to also inhibit UCH-L3 and USP2 iso2 to a lesser degree than IsoT, and UCH-1 and USP7 at micromolar levels. The inhibitor was selective for isopeptidase activity as no inhibition was observed for a panel of cysteine proteases (data not shown). Further support for direct inhibition of IsoT protease activity was obtained using a tetra-ubiquitin cleavage assay followed by Western analysis using an anti-Ub antibody. The results indicated that there is a nice dose-response for inhibition of tetra-ubiquitin as the compound is titrated. As the molar concentration of Compound A is increased, there is a decrease in the level of free (cleaved) ubiquitin generated. The apparent $IC_{50}$ is approximately 100 nM, which correlates nicely with the observed $IC_{50}$ for IsoT inhibition in the biochemical assay. These data further support that inhibition of HIV replication by the compound was due to inhibition of IsoT activity. Details of the high throughput screen design as well as materials and methods employed in the screen are detailed below.

IsoT High-Throughout Screen Design: The assay design is based on the method of Dang et al. (Biochemistry. 37:1868-79, 1998), further optimized for ultra-HTS in 1536-well format. Briefly, isopeptidase activity is detected through the liberation of AMC from the ubiquitin-AMC substrate and is measured by a fluorescent signal. In the presence of an inhibitor compound or ubiquitin aldehyde, protease activity is inhibited: 5 µL/well of 360 pM IsoT in complete reaction buffer (20 mM HEPES, 0.5 mM EDTA, 1 mg/ml BSA, 10 mM DTT, pH7.8) is dispensed into a black solid non-TC 1536-well plate (Greiner Bio-one, Cat# 789176) by a custom BottleValve liquid dispenser, 50nL 1 mM compounds and controls (Ub-aldehyde) are transferred using our in-house built PinTool (10 µM final compound concentration), and the interaction is allowed to proceed for 3 hrs at 37° C. 1 µL of 300 nM Ub-AMC is then dispensed and the reaction incubated for 20 minutes at 37° C. Fluorescence intensity is measured using a ViewLux plate reader (PerkinElmer). Compound titrations for dose-responses and $IC_{50}$ determinations are carried out using a Minitrak apparatus (Packard BioScience) for half-log serial dilutions in DMSO.

Production of IsoT Enzyme: IsoT was cloned into pRSETa using standard cloning procedures and transformed into strain BL21 (DE3). Protein expression was done as previously described (Lesley et al., 2002), with the exception that protein expression was induced with 1 mM IPTG. Protein purification was done as follows: 4 grams of cell pellet was resuspended in 40 ml of Lysis Buffer consisting of 50 mM Tris-HCl, 50 mM NaCl, 10 mM imidazole, pH 7.9, and sonicated for 4×1 minute. After a 20 minute spin at 15,000×g, the cleared lysate was poured onto a column containing 1.5 ml bed volume of Chelating-sepharose FastFlow (Amersham) charged with Nickel. The column was washed with 7.5 ml of Wash Buffer consisting of 50 mM Tris-HCl, 300 mM NaCl, 40 mM imidazole and 10% glycerol, pH 7.9. The protein was eluted with 4.5 ml of Elution Buffer consisting of 20 mM Tris-HCl, 300 mM imidazole, 10% glycerol, pH 8.0.

Testing of IsoT inhibitors against HIV-IIIb: Compounds diluted in DMSO from the IsoT screen were arrayed starting at 1 mM in 384-well polypropylene compound plates (Greiner) and then half-log serially diluted in DMSO for a total of 8 points using the Minitrak apparatus (Packard Bioscience). HeLaCD4βgal cells (1500/50 µL/well) were seeded into 384-well white plates (Greiner), and after overnight adherence, 500 nL of compounds were transferred into 3 replicate cell plates using the Minitrak (Packard Bioscience) for infectivity and cytotoxicity testing, resulting in a final compound dilution series starting at 10 µM. After 30 minutes, HIV-IIIb (16 ng/10 µL/well) was added to the infectivity testing cell plates. On Day 3 following compound and virus addition, infection was assessed by adding 50 µL of Gal Screen (Applied Biosystems) to the infected cells and reading luminescence after 1 hour on the CLIPR (Molecular Devices). Cytotoxicity was assessed by adding 50 µL of a 1:4 dilution of Cell Titer Glo (Promega) to the uninfected cells and reading after 1 hour on the CLIPR. Dose response measurements were interpreted using the standard sigmoidal dose-response equation. A in-house generated curve fitting computer program was used in $IC_{50}$ calculations.

Inhibition of tetra-ubiquitin (Ub4) cleavage by IsoT inhibitors: IsoT was diluted to a final concentration of 760 pM in reaction buffer (20 mM HEPES, 0.5 mM EDTA, 1 mg/mL BSA, 10 mM DTT, pH=7.8) and 18 µL was added to each of 9 eppendorff tubes. Compound 2096 was half-log serially diluted starting at 200 µM in DMSO for a total of 8 points, and 1 µL of each dilution was then added to a tube of IsoT, resulting in a dilution series starting at 10 µM in the assay tube. As a control for maximal cleavage, one tube received 1 µL of DMSO alone. After 30 minutes of incubation at 37° C., 1 µL of a 250 µg/mL solution of tetra-Ubiquitin (Ub4; Biomol) in reaction buffer was added to each tube, and the tubes were then incubated for an additional 18 hours at 37° C. Denaturing protein sample buffer (Invitrogen) was then added, and all samples were boiled and then loaded onto a 4-to-12% NuPage bis-Tris gel (Invitrogen) and subjected to gel electrophoresis as suggested by the manufacturer. Following transfer to nitrocellulose, blots were blocked with 5% nonfat milk in PBST (phosphate buffered saline with 0.05% Tween 20) and then subjected to immunoblotting with a rabbit polyclonal antibody against Ubiquitin (1:1000 dilution in 5% nonfat milk in PBST; Upstate) followed by HRP-conjugated goat-anti-rabbit secondary antibody (1:3000 dilution in 5% nonfat milk in PBST; Southern Biotechnologies). Bands were then visualized using ECL-plus detection reagent (Amersham).

It is understood that the examples and embodiments described herein are for illustrative purposes only and that various modifications or changes in light thereof will be suggested to subjects skilled in the art and are to be included within the spirit and purview of the application and scope of the appended claims. Although any methods and materials similar or equivalent to those described herein can be used in the practice or testing of the present invention, the preferred methods and materials are described.

All publications, GenBank sequences, patents and patent applications cited herein are hereby expressly incorporated by reference in their entirety and for all purposes as if each is individually so denoted.

We claim:

1. A method for inhibiting HIV replication in an HIV-infected cell, the method comprising contacting the cell with a compound which down-regulates expression of an IsoT-encoding gene; thereby inhibiting HIV replication in the cell.

2. The method of claim 1, wherein the IsoT is a human IsoT.

3. The method of claim 1, wherein the compound inhibits HIV replication in an IsoT-expressing cell in vitro.

4. The method of claim 3, wherein the compound is selected from the group consisting of a short interfering RNA (siRNA), an anti-sense nucleic acid, and a complementary DNA (cDNA).

5. The method of claim 4, wherein the compound is a siRNA against IsoT.

* * * * *

SEQUENCE LISTING

```
<160> NUMBER OF SEQ ID NOS: 6

<210> SEQ ID NO 1
<211> LENGTH: 21
<212> TYPE: RNA
<213> ORGANISM: Artificial Sequence
<220> FEATURE:
<223> OTHER INFORMATION: siRNA against Homo sapiens IsoT

<400> SEQUENCE: 1
aguucaccuu cggcuuagau u                                                   21

<210> SEQ ID NO 2
<211> LENGTH: 21
<212> TYPE: DNA
<213> ORGANISM: Artificial Sequence
<220> FEATURE:
<223> OTHER INFORMATION: siRNA against Homo sapiens IsoT

<400> SEQUENCE: 2
ggcagauggg ugaucuacat t                                                   21

<210> SEQ ID NO 3
<211> LENGTH: 21
<212> TYPE: RNA
<213> ORGANISM: Artificial Sequence
<220> FEATURE:
<223> OTHER INFORMATION: siRNA against Human Immunodeficiency Virus Vpr

<400> SEQUENCE: 3
ggaguggaag ccauaauaau u                                                   21

<210> SEQ ID NO 4
<211> LENGTH: 21
<212> TYPE: RNA
<213> ORGANISM: Artificial Sequence
<220> FEATURE:
<223> OTHER INFORMATION: siRNA against HIV Vpr

<400> SEQUENCE: 4
acaacugcug uuuauccauu u                                                   21

<210> SEQ ID NO 5
<211> LENGTH: 21
<212> TYPE: DNA
<213> ORGANISM: Artificial Sequence
<220> FEATURE:
<223> OTHER INFORMATION: siRNA against HIV Tat

<400> SEQUENCE: 5
cugcuuguac caauugcuat t                                                   21
```

-continued

```
<210> SEQ ID NO 6
<211> LENGTH: 21
<212> TYPE: DNA
<213> ORGANISM: Artificial Sequence
<220> FEATURE:
<223> OTHER INFORMATION: siRNA against HIV Tat

<400> SEQUENCE: 6
gccuuaggca ucuccuaugt t                                            21
```